United States Patent
Maitland et al.

(10) Patent No.: US 11,369,385 B2
(45) Date of Patent: *Jun. 28, 2022

(54) SHAPE MEMORY POLYMER VESSEL OCCLUSION DEVICE

(71) Applicants: THE TEXAS A&M UNIVERSITY SYSTEM, College Station, TX (US); SHAPE MEMORY MEDICAL, INC, Santa Clara, CA (US)

(72) Inventors: Duncan J. Maitland, College Station, TX (US); Todd L. Landsman, San Jose, CA (US); Jennifer N. Rodriguez, Fremont, CA (US); Anthony J. Boyle, College Station, TX (US); Alan C. Glowczwski, College Station, TX (US); Mark A. Wierzbicki, College Station, TX (US)

(73) Assignees: THE TEXAS A&M UNIVERSITY SYSTEM, College Station, TX (US); SHAPE MEMORY MEDICAL, INC, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,270

(22) Filed: Sep. 25, 2020

(65) Prior Publication Data
US 2021/0015485 A1    Jan. 21, 2021

Related U.S. Application Data

(63) Continuation of application No. 15/754,330, filed as application No. PCT/US2016/050097 on Sep. 2, 2016, now Pat. No. 10,786,261.
(Continued)

(51) Int. Cl.
*A61B 17/12* (2006.01)
*A61B 17/00* (2006.01)

(52) U.S. Cl.
CPC ...... *A61B 17/1219* (2013.01); *A61B 17/1215* (2013.01); *A61B 17/12109* (2013.01);
(Continued)

(58) Field of Classification Search
CPC .......... A61B 17/1219; A61B 17/12109; A61B 17/1215; A61B 17/12172; A61B 17/0057;
(Continued)

(56) References Cited

U.S. PATENT DOCUMENTS 5,980,514 A * 11/1999 Kupiecki ......... A61B 17/12145 606/32
6,123,715 A  6/2000 Amplatz
(Continued)

FOREIGN PATENT DOCUMENTS

CN  1671330  9/2005
CN  101479006  7/2009
(Continued)

OTHER PUBLICATIONS

Chinese Patent Office, First Office Action and Search Report dated Apr. 16, 2020 in Chinese patent application No. 01680064779.0, 20 pages total.
(Continued)

*Primary Examiner* — Erich G Herbermann
(74) *Attorney, Agent, or Firm* — Trop, Pruner & Hu, P.C.

(57) ABSTRACT

An embodiment includes a system comprising: an outer conduit; a shape memory polymer (SMP) foam; a metal backbone including: (a)(i) a first portion that extends from the SMP foam proximal end to the SMP foam distal end and which is generally covered by the SMP foam, and (a)(ii) a distal portion that extends distally from the SMP foam distal end and which is not covered by the SMP foam; wherein: (b)(i) SMP foam and the metal backbone are both included within the outer conduit adjacent to the outer conduit distal
(Continued)

end; (b)(ii) the metal backbone distal portion transitions from a secondary shape that is uncoiled to a primary shape that is coiled; and (b)(iii) the metal backbone distal portion is in the metal backbone distal portion secondary shape and is located between the SMP foam distal end and the distal end of the outer conduit.

19 Claims, 7 Drawing Sheets

Related U.S. Application Data

(60) Provisional application No. 62/214,767, filed on Sep. 4, 2015.

(52) U.S. Cl.
CPC ............ *A61B 17/12172* (2013.01); *A61B 2017/00526* (2013.01); *A61B 2017/00871* (2013.01); *A61B 2017/00898* (2013.01); *A61B 2017/12063* (2013.01)

(58) Field of Classification Search
CPC ........ A61B 2017/00526; A61B 2017/00871; A61B 2017/00898; A61B 2017/12063; A61B 2017/00623; A61B 2017/00606; A61B 2017/00592; A61F 2/064; A61F 2210/0014; A61F 2210/0033
See application file for complete search history.

(56) References Cited

U.S. PATENT DOCUMENTS

| | | |
|---|---|---|
| 2001/0025155 A1 | 9/2001 | Yoon |
| 2002/0068950 A1 | 6/2002 | Corcoran et al. |
| 2003/0236533 A1 | 12/2003 | Wilson et al. |
| 2005/0065547 A1 | 3/2005 | Marino et al. |
| 2005/0234509 A1 | 10/2005 | Widomski et al. |
| 2006/0009785 A1 | 1/2006 | Maitland et al. |
| 2006/0116713 A1 | 6/2006 | Sepetka et al. |
| 2006/0122646 A1 | 6/2006 | Corcoran et al. |
| 2006/0135947 A1 | 6/2006 | Soltesz et al. |
| 2007/0010851 A1 | 1/2007 | Chanduszko et al. |
| 2009/0056722 A1* | 3/2009 | Swann .................. A61B 90/39 128/831 |
| 2010/0324585 A1 | 12/2010 | Miles et al. |
| 2011/0144686 A1* | 6/2011 | Wilson ............. A61B 17/12022 606/191 |
| 2012/0172973 A1 | 7/2012 | Deckard et al. |
| 2013/0231684 A1 | 9/2013 | Aurilia et al. |
| 2013/0253086 A1 | 9/2013 | Wilson et al. |
| 2013/0253634 A1 | 9/2013 | Wilson et al. |
| 2013/0317541 A1* | 11/2013 | Singhal ............. C08G 18/3278 606/213 |
| 2014/0371789 A1 | 12/2014 | Hariton et al. |
| 2018/0132856 A1 | 5/2018 | Wierzbicki et al. |

FOREIGN PATENT DOCUMENTS

| | | |
|---|---|---|
| CN | 102186426 | 9/2013 |
| EP | 2248486 A2 | 10/2010 |
| JP | 2018526128 | 9/2018 |
| WO | 2005053547 A2 | 6/2005 |

OTHER PUBLICATIONS

Japanese Patent Office, Notice of Reason(s) for Rejection dated Jan. 14, 2020 in Japanese Patent Application No. 2019-078450, 10 pages total.

European Patent Office, Extended European Search Report dated Apr. 26, 2019 in European Patent Application No. 16843059.3.

Singhal, et al., "Low density biodegradable shape memory polyurethane foams for embolic biomedical applications," Acta Biomaterial, Jan. 2014, pp. 67-76, vol. 10, issue 1, Elsevier Ltd.

Japan Patent Office, Notice of Reason(s) for Rejection dated Jan. 8, 2019 in Japanese Patent Application No. 2018-511680, eight pages.

European Patent Office, Communication pursuant to Rules 70(2) and 70a(2) EPC dated Jan. 8, 2019, in European Patent Application No. 16783914.1, 12 pages.

The International Searching Authority, "Notification of Transmittal of the International Search Report and the Written Opinion of the International Searching Authority", dated Jul. 28, 2016 in International Application No. PCT/US2016/028789, 16 pages.

Wierzbicki, et al.; "Mechanical and in vitro evaluation of an experimental canine patent ductus arteriosus occlusion device", available on-line Dec. 21, 2015, pp. 156-167, Journal of the Mechanical Behavior of Biomedical Materials 59, Elsevier Ltd.

The International Searching Authority, Written Opinion of the International Searching Authority and the International Search Report dated Nov. 21, 2016 in International Application No. PCT/US16/50097, seven pages.

Singhal et al., "Ultra Low Density and Highly Crosslinked Biocompatible Shape Memory Polyurethane Foams." Journal of Polymer Sciences B Polymer Physics, May 15, 2012, pp. 1-27, vol. 50, Issue 10, National Institutes of Health.

Wikipedia, "Pseudoelasticity," Aug. 30, 2016, 2 pages, https://en.wikipedia.org/wiki/Pseudoelasticity.

Wikipedia, "Cone," Aug. 30, 2016, 6 pages, https://en.wikipedia.org/wiki/Cone.

Landsman et al., "Design and verification of a shape memory polymer peripheral occlusion device," Journal of the Mechanical Behavior of Biomedical Materials, Jun. 23, 2016, pp. 195-206, vol. 63, Elsevier Ltd.

Rodriguez et al., "Reticulation of low density shape memory polymer foam with an in vivo demonstration of vascular occlusion," Journal of the Mechanical Behavior of Biomedical Materials, Aug. 11, 2014, pp. 102-114, vol. 40, Elsevier Ltd.

* cited by examiner

SHAPE MEMORY POLYMER VESSEL OCCLUSION DEVICE

PRIORITY CLAIM

This application is a continuation of U.S. patent application Ser. No. 15/754,330, filed Feb. 22, 2018, which is a § 371 national stage of international application PCT/US2016/050097, which filed Sep. 2, 2016, which claims priority to United States Provisional Patent Application No. 62/214,767 filed on Sep. 4, 2015 and entitled "Shape Memory Polymer Vessel Occlusion Device." The content of each of the above applications is hereby incorporated by reference.

STATEMENT REGARDING FEDERALLY SPONSORED RESEARCH OR DEVELOPMENT

This invention was made with government support under R01EB000462 awarded by National Institutes of Health National Institute of Biomedical Imaging and Bioengineering. The government has certain rights in the invention

BACKGROUND

An estimated 6 million people in the United States suffer from severe symptoms of chronic venous insufficiency. Symptoms range from dramatic skin changes to painful recalcitrant ulcers that are often found in the lower extremities. Chronic venous insufficiency is caused by weakened venous valves that can no longer prevent backflow in peripheral veins that carry blood to the heart resulting in a sudden rise in venous pressure. This hypertension can lead to the formation of varicose veins as well as venous ulcers. The greater saphenous vein is the most common region treated for chronic venous insufficiency. Previous methods of treatment of the manifestations of chronic venous insufficiency include manual compression, surgical ligation and stripping, sclerotherapy, and endovenous ablation of the greater saphenous vein. Endovenous ablation has many downfalls. With endovenous ablation the patient experiences pain, either from the anesthetic injections or from the laser treatment. Further, recanalization may occur as the physician must uniformly ablate the whole cross-section of the vein and control the laser's pull-back speed. Many other complications may result such as deep vein thrombosis, bruising, dysesthesia, skin burns, bruising, thrombophlebitis, and nerve damage.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
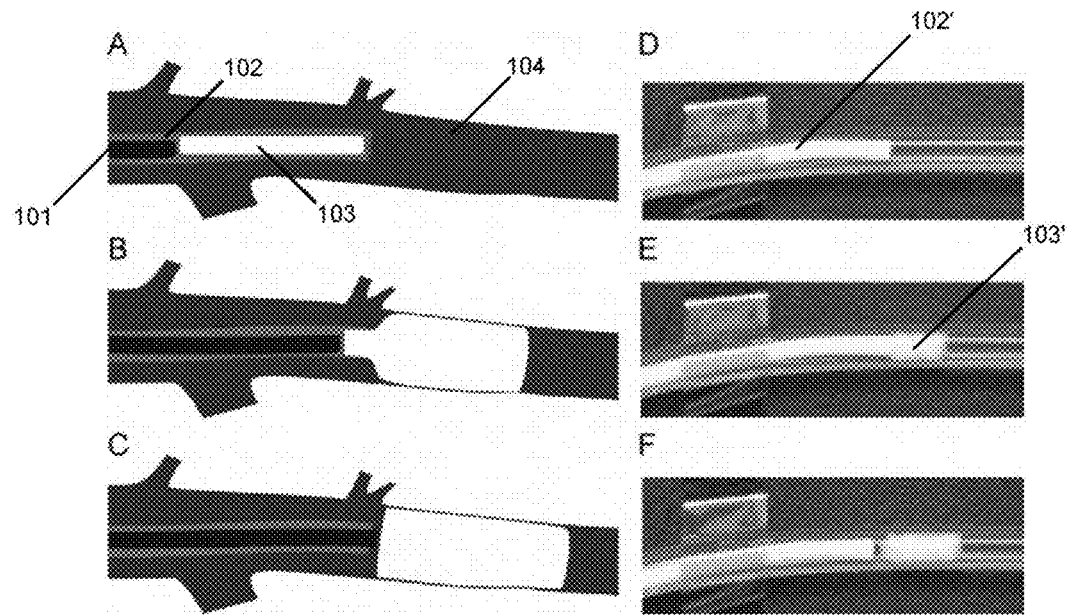
FIGS. 1(A)-(C) and (D)-(F) depict deployment of embodiments.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner "Connected" may indicate elements are in direct physical or electrical contact with each other and "coupled" may indicate elements co-operate or interact with each other, but they may or may not be in direct physical or electrical contact.

An embodiment provides a minimally invasive approach to achieve complete occlusion of arteries and veins within the peripheral vasculature. The cost, complexity, recurrence, risk, and complications of peripheral embolizations make the embodiments discussed herein highly desirable.

An embodiment uses polyurethane shape memory polymer (SMP) foam to selectively occlude regions of vasculature where persistent blood flow may cause complications. The morphology and chemistry of the foam allows it to be compressed and loaded into an introducer and advanced through a catheter to the target region. Upon contact with circulating blood, the foam expands (e.g., within 2, 4, 6, 8, or 10 minutes after contacting blood) to its original geometry and completely fills the vessel lumen. The procedure utilizes minimally invasive techniques.

An embodiment includes one or more anchors placed proximal, distal, or at both locations relative to the device. The anchor(s) holds the device in place within the blood vessel. In certain embodiments, the anchor(s) is made of nitinol and/or platinum alloys.

Additionally, in an embodiment an object (e.g., catheter, expanding balloon catheter) is used to guide the device to the location (at the urging of a guide wire) in the blood vessel requiring treatment. This allows for the device to fully expand within the vessel with minimal blood flow to the location of the implant.

An embodiment of the SMP vessel occlusion device may utilize a number of delivery mechanisms. One such mechanism is a core wire that is placed within the volume of the foam implant and the implant is crimped over the core wire to create friction between the implant and core wire. The friction allows retraction and advancement of the device until it is fully expanded in the lumen of the treatment vessel. Once the device is fully expanded the friction is reduced enough to allow the core wire to be retracted through the volume of the device.

Another such delivery mechanism is one in which the device is simply advanced through the catheter with a guidewire or pusher mechanism until the device is completely ejected from the delivery catheter. Such an embodiment may only include the foam without a core wire. The embodiment may be coupled with an anchor(s) (e.g., nitinol mesh) implanted separately from the foam upstream and/or downstream of the foam.

Another delivery mechanism is one in which the proximal end of the device is attached to a pusher mechanism via an exposed stainless steel wire. When the device is delivered to the target vessel, an electrical current is applied to the pusher mechanism which causes electrolysis of the exposed stainless steel wire-effectively releasing the implant from the pusher mechanism.

Embodiments of vascular occlusion devices discussed herein have a wide variety of indications, including the management of pelvic venous congestion, varicocele, varicosities associated with portal vein hypertension, traumatic hemorrhage, splenic artery aneurysms, and chronic venous insufficiency (CVI). In each of these conditions, blood flow through specific vascular pathways presents potentially life-threatening consequences and extreme amounts of pain. In these instances, physicians rely on occlusive devices to divert blood flow from susceptible vessels and minimize adverse outcomes. More generally, embodiments are useful for solve any manner of vascular issue brought on by a vascular anomaly. Even more generally, the foam systems may be used to block flow in non-biological contexts. For example, foams (coupled to one or more anchors in some embodiments) may be used in general plumbing contexts or to otherwise quickly block fluid flow (where fluid flow may entail liquid or gas state flow).

An embodiment is directed to an embolic device, wherein the device is used to stably occlude the flow of blood within a vessel undergoing treatment. In the embodiment, the clot formation and stable occlusion occurs within 0-30 minutes after deployment of the device. For example, based on HDI content occlusion may occur in less than 60 seconds from the time the foam is deployed from the catheter. The device is typically delivered and deployed in the treatment region in a time frame of 5 seconds to 30 minutes. More than one device may be required and/or chosen to achieve complete vessel occlusion.

In an embodiment, the device is composed of a polyurethane SMP. In certain embodiments, the polymer is selected from N,N,N',N'-Tetrakis (2-hydroxypropyl) ethylenediamine (HPED); 2,2',2"-nitrilotriethanol (TEA); 1,6-diisocyanatohexan (HDI); and trimethylhexamethylene diisocyanate (2,2,4- and 2,4,4-mixture) (TMHDI).

In an embodiment, the occlusion of a blood vessel occurs as a result of flow stagnation of the blood caused by the morphology of the device. The occlusion also occurs as a result of the tissue injury response of the endothelium of the vessel to the implantation of the device and the exposure of tissue factor binding sites.

In certain embodiments, the occlusion occurs as a result of recirculation zones within the blood flow caused by the morphology of the implant. In other embodiments, the occlusion occurs as a result of platelet aggregation and activation throughout the volume of the device.

During in vitro blood flow studies, complete occlusion of the foam device was observed at 270 seconds. Complete occlusion was evidenced by flow diverting through a pressure relief valve. At this point, the pressure within the vein model created by thrombus formation exceeded the pressure relief valve setting and flow was diverted through the bypass pathway. Results show blood is penetrating throughout the entire volume of the foam device, demonstrating the effectiveness of foam cell reticulation in creating interconnected pathways along the length of the device. After 30 seconds of blood perfusion, each cross section of the foam consisted of primarily erythrocytes enmeshed in loose, interspersed fibrin. At 270 sec, approximately 50% of the proximal section of foam consisted of dense fibrin, which likely contributed to the complete vessel occlusion which occurred at this time point.

An embodiment is directed to a delivery mechanism which delivers the embolic device to an area needing treatment. In certain embodiments, the delivery vehicle is a catheter, expanding balloon catheter, or a guidewire. When the delivery vehicle is a guidewire, in some embodiments the device is crimped over the core wire to provide sufficient friction between the implant and core wire to allow retraction and advancement of the device until it is fully expanded in the lumen of the treatment vessel. The core wire is selected from stainless steel, nitinol, steel alloy, polypropylene, polytetrafluoroethylene, or nylon wire, or a combination of these materials comprising a braided wire or coil. In some embodiments, the core wire is between 0.0005 and 0.050 inches in diameter.

An embodiment provides a minimally invasive approach to achieve complete occlusion of blood vessels and prevent recurrence through the use of nitinol anchors on the proximal and distal ends of a polyurethane SMP foam. While the SMP foam encourages rapid hemostasis and healing, the device anchors ensure the foam remains in the treated vessel, minimizing the risk of embolization downstream of the target vessel and device migration.

Material modifications such as plasma surface treatments, adding radiopaque fillers, and heat treating can be employed to minimize the time to hemostasis, optimize the design and dimensions of the device, ensure each component possesses adequate mechanical strength to prevent device fracture and dislocation from the target region, and to evaluate the deliverability, efficacy, and visualization of the device, via ultrasonography or X-ray in an in vitro model of a human great saphenous vein (GSV).

An embodiment uses polyurethane SMP foam that is actuated at 37° C. (although other embodiments actuate at 36, 38, 39° C. or more), which means no external heating source is required to expand the foams after implantation. However, another embodiment has a higher transition temperature that requires the device to be actively heated via, for example, heated saline injection, radiofrequency heating, and/or laser heating to initiate expansion.

In an embodiment, the SMP vessel occlusion device is delivered using minimally invasive endovascular techniques in order to selectively occlude regions of vasculature where undesired persistent blood flow may cause complications. A SMP foam is crimped over a core wire and attached to a pusher system that allows the device to be navigated through the lumen of the catheter in order to reach the target site. Upon contact with blood, the device expands and resumes its pre-crimped geometry. This allows for a window of time between zero to thirty minutes for the delivery of the device to the treatment region. The foam expands upon exiting the catheter in order to fill the entire cross-section of the vessel. Once the foam completely expands, the pusher system can be retracted due to less friction between the foam and the core wire. This allows the pusher system and catheter to be removed while leaving the foam implant in place. In an embodiment thrombosis occurs within the entire volume of foam within 0 to 90 minutes. The porous morphology of the implant initiates the clotting cascade by creating many recirculation zones and flow stagnation in the blood stream. The clotting cascade is further stimulated by the expansion of the foam implant which damages the endothelium and exposes tissue factor binding sites. The expansion of the foam implant also triggers the foreign body response.

An embodiment uses a pure foam device whereby a SMP foam is synthesized, reticulated, cut to the desired geometry using biopsy punches, mechanically conditioned using a heated stent crimper, dried in a freeze-dryer, and then crimped to its deliverable geometry. This allows the foam device to be delivered to the target region via an introducer, catheter, and guidewire.

Another embodiment is directed towards areas of high flow including, but not limited to, arterial flow. An internal elastic wire that optionally runs through the middle of the foam is laser welded or epoxied to the external surface of the distal anchor. The proximal anchor is attached in the same manner as the distal anchor.

Another embodiment contains anchors proximal, distal, or in both locations relative to the SMP foam. The anchors contain a longitudinal member that is inserted centrally through a cylinder of SMP foam, which is then coated with a neat polymer solution consisting of a combination of N,N,N',N'-Tetrakis(2-hydroxypropyl)ethylenediamine (HPED), 2,2',2''-nitrilotriethanol (TEA), 1,6-diisocyanato-hexan (HDI), and trimethylhexamethylene diisocyanate (2,2,4- and 2,4,4-mixture) (TMHDI) that acts as an epoxy attaching the SMP foam to the coil backbone. The neat polymer solution may itself constitute a SMP (which may be foams or may not be foamed).

Foam and Device Synthesis

Various versions of SMP foam have been fabricated. For example, one version contains 100% hexamethylene diisocyanate (HDI) and another contains a mixture of HDI and trimethylhexamethylene diisocyanate (2,2,4- and 2,4,4-mixture) (TMHDI) for the isocyanate monomer in the polyurethane reaction. The less hydrophobic 100% HDI foam was made specifically for vessel implantation to allow for immediate self-actuation of the VOD in vivo without the need for external heating. The foam actuates at body temperature after exposure to moisture in the blood which causes a drop in the material's transition temperature. Both foams were reticulated and chemically post-processed in the same manner Aside from their different hydrophobicities, these two foams share very similar mechanical properties and shape memory characteristics. During the foaming process, the material is constrained by the side walls of the container and unconstrained from above as it rises. Due to these conditions and their ultra-low densities, the foams may have an anisotropic morphology.

In greater detail and as detailed in Landsman et al., Design and Verification of a Shape Memory Polymer Peripheral Occlusion Device, Journal of the Mechanical Behavior of Biomedical Materials 63 (2016): 195-206, foams were fabricated as follows (although other methods may be used). Isocyanate (NCO) prepolymers were synthesized with appropriate molar ratios of N,N,N',N'-Tetrakis(2-hydroxypropyl)ethylenediamine (HPED, 99%; Sigma-Aldrich Inc., St. Louis, Mo.), triethanolamine (TEA, 98%; Sigma-Aldrich Inc.), and hexamethylene diisocyanate (HDI, TCI America Inc., Portland, Oreg.). The prepolymers were reacted for 2 days with a temperature ramp from room temperature to 50° C. at a rate of 20° C./hr, held isothermally at 50° C. for 16 hours, and passively allowed to cool back to room temperature. A hydroxyl (OH) mixture was blended with the remaining molar equivalents of HPED and TEA. This mixture also contained deionized (DI) water (>17 MΩcm purity; Millipore water purifier system; Millipore Inc.), and catalysts (T-131 and BL-22, Air Products and Chemicals, Inc., Allentown, Pa.). During the foaming step, the NCO prepolymer and the OH mixture were combined in a foaming cup along with surfactants (DC 198 and DC 5943, Air Products and Chemicals, Inc., Allentown, Pa.) and the physical blowing agent, Enovate 245fa (Honeywell International, Inc., Morristown, N.J.). This solution was mixed in a FlackTek Speedmixer (FlackTek, Inc., Landrum, S.C.) and poured into a bucket to form a foam. The foam was cured at 60° C. for 5 minutes before passively cooling to room temperature for further processing. Various foam formulations and pore sizes were fabricated to create foams with differing crosslink densities, glass transition temperatures (Tg), rate of moisture plasticization, and subsequent foam expansion rates. Foam formulations are denoted as H20-H60, where the numerical value appearing after "H" corresponds to the ratio of HPED to TEA equivalents in the polymer premix. Both foam formulation and pore size were used to control the expansion rate of the foams and the resultant working time to enable catheter delivery.

After fabrication, foams were cut into blocks 2 cm thick, 7 cm long, and 6 cm wide. These blocks were then reticulated using the same method described previously (Rodriguez, J.; Miller, M.; Boyle, A.; Horn, J.; Yang, C.; Wilson, T.; Ortega, J.; Small, W.; Nash, L.; Skoog, H.; and Maitland, D., Reticulation of low density SMP foam with an in vivo demonstration of vascular occlusion, Journal of the Mechanical Behavior of Biomedical Materials 40 (2014): 102-114). In short, the foams were penetrated by a floating pin array while subjected to low amplitude, high frequency perturbations, which allowed the creation of pinholes in the foam pore membranes. These pinholes create interconnected pores throughout the foam which allow blood flow and eventual connective tissue deposition to penetrate throughout the entire device.

After reticulation, the foams were cut with disposable biopsy punches (Sklar Surgical Instruments, West Chester, Pa., USA) for three different device sizes—6, 8, and 12 mm. These device sizes were used to enable delivery through 4, 5, and 6 Fr catheters, respectively, and the ability to treat vessels with diameters between approximately 2-11 mm After the foams were cut into their final geometry, they were cleaned to remove any plasticizers and unreacted monomers from the foams. Each cleaning cycle lasted 15 minutes and was performed under sonication in a 40° C. water bath. The first two cleaning cycles consisted of submerging the foams in 99% isopropyl alcohol (VWR, Radnor, Pa.). Then the foams were rinsed with reverse osmosis (RO) water before being cleaned in four cycles of Contrad 70 liquid detergent (Decon Labs, King of Prussia, Pa.). Each foam was then rinsed with RO water until no Contrad 70 residue was evident. Finally, the foams were cleaned for two cycles in RO water. After cleaning, the damp foams were frozen in a −20° C. freezer for 12 hours before freeze-drying in a FreeZone Freeze Dryer (Labconco, Kansas City, Mo.) for 24 hours.

Due to the low radial force of the SMP foams, a coil anchor is incorporated into some embodiments of the peripheral embolic device (PED) to enable implantation in both arteries and veins with minimal risk of device migration. To fabricate the coil anchors used for in vitro device verification tests, 0.018" diameter 90/10% platinum/iridium coils with an inner diameter of 0.010" were threaded over 0.005", 0.006", and 0.008" diameter superelastic nitinol wire for the 6, 8, and 12 mm PED devices, respectively. The coils were then wrapped around a stainless steel mandrel that had been machined to each device diameter and shape-set in a 550° C. furnace for 15 minutes. After 15 minutes, the mandrels were immediately quenched in room temperature water to set the final shape of the coil. The coils were removed from the mandrel and a straight section of the coil was manually threaded through the center of the foam before crimping. While immediately above the platinum/iridium coil includes a channel to receive the nitinol wire in other embodiments the platinum/iridium coil and nitinol wire are merely coupled to each other.

Mechanical Characterization of the Foams

Mechanical testing of SMP foams was performed in compression mode according to ASTM D1621-10 Standard Test Method for Compressive Properties of Rigid Cellular Plastics using the Instron load frame with a 500 N load cell at ambient laboratory temperatures 23±2° C. Cylindrical samples 25.4 mm in diameter by 25.4 mm tall of both the non-reticulated and reticulated (chemically etched or not etched) foams were prepared. These samples were frozen in a −80° C. freezer overnight and subsequently lyophilized for 24 hours prior to mechanical testing. To assess the effects of pin mass, uni-axial versus tri-axial reticulation, and chemical etching, nine different reticulation schemes (including a non-reticulated control) were investigated as outlined in Table 1. Five (5) samples were tested for each version. At least some of the reticulation schemes and methods addressed herein are further addressed in greater detail in Rodriguez, J.; Miller, M.; Boyle, A.; Horn, J.; Yang, C.; Wilson, T.; Ortega, J.; Small, W.; Nash, L.; Skoog, H.; and Maitland, D., Reticulation of low density SMP foam with an in vivo demonstration of vascular occlusion, Journal of the Mechanical Behavior of Biomedical Materials 40 (2014): 102-114.

TABLE 1

| | Nitinol pin mass | Chemical etch | Number of samples tested |
|---|---|---|---|
| Uni-axial | 1 g axial | No | 5 |
| | 1 g axial | Yes | 5 |
| | 2 g axial | No | 5 |
| | 2 g axial | Yes | 5 |
| Tri-axial | 1 g axial, 1 g trans-axial | No | 5 |
| | 1 g axial, 1 g trans-axial | Yes | 5 |
| | 2 g axial, 1 g trans-axial | No | 5 |
| | 2 g axial, 1 g trans-axial | Yes | 5 |
| Non-reticulated control | Not applicable | No | 5 |

In Vivo Vascular Occlusion Assessment

Uni-axial and tri-axial reticulated SMP foam samples were cut into 20-30 mm long cylindrical samples using a 10 mm diameter biopsy punch. The samples were pre-conditioned by radially compressing to 1 mm diameter using a SC250 stent crimper (Machine Solutions Inc., Flagstaff, Ariz.) at 97° C. and heated to expand to their original shape. The SMP foam cylinders were then chemically etched, rinsed, and cleaned. The samples were dried in vacuum and stored in an air-tight container with desiccant. The cylindrical samples were cut to 8 mm diameter using fine-tip scissors and 10 mm long using a razor blade. Samples were then radially compressed to the minimum diameter of approximately 1 mm using the stent crimper at 97° C., cooled under compression to maintain the compressed shape, and stored in an air-tight container with desiccant until implantation in vivo.

Six (6) devices (3 uni-axial and 3 tri-axial reticulated using 1 g pins and etching) were successfully deployed into multiple hind limb vessels of a three month old, 25 kg pig. Angiography performed prior to implantation of the VODs indicated the diameters of the vessels were on average 2.6 mm in diameter, which was smaller than the 8-mm diameter of the uncompressed VODs; therefore, the devices were able to expand to approximately 33% of their original diameter. A 5F catheter, 0.055" inner diameter, was navigated to the implant site using a 0.035" guidewire. The compressed foam VOD was submerged in room temperature saline for 2-5 min and then submerged in 32° C. saline for 3-5 s. The device was placed inside the catheter for 5 min to allow the foam to begin expanding and then pushed out of the catheter using the 0.035" guidewire (FIGS. 1A to 1C). This procedure resulted in expansion of the foam immediately as it emerged out of the catheter as shown in a preliminary benchtop in vitro demonstration (FIGS. 1D to 1F). Contrast enhanced fluoroscopy was used to determine when the device had been deployed, by observing the location of the guidewire and if possible, a lack of contrast agent in the vessel. After delivery into the vessel, the device expanded to its primary shape and subsequently blocked the vessel. The vessel occlusion time was defined as the time after device delivery until injected contrast agent ceased to flow through or past the device; at that point clotting is likely to have occurred. Vessel occlusion time was determined via iodinated contrast injections visualized with angiography 45 s after deployment and then at 30 s intervals thereafter.

In Vivo Vascular Occlusion

The uni-axial reticulated foam had an average occlusion time of 90±11 s and the tri-axial reticulated foam had an average occlusion time of 128±77 s. On average, the uni-axial reticulated foam induced faster occlusion that the tri-axial reticulated foam. This result is not unexpected since blood flow is likely impeded more by the less reticulated foam, potentially resulting in more rapid clotting due to increased flow stagnation and surface area. Due to the great difference in occlusion time exhibited by the tri-axial foam relative to the uni-axial foam, the effects of the extent of reticulation on occlusion time are still being investigated.

FIG. 1 shows a schematic diagram of endovascular deployment of and embodiment of the SMP foam vascular occlusion device (VOD): (A) the device is pushed near the 5F catheter tip (distal end of the catheter) by the guidewire 101, (B) the guidewire pushes the self-actuating device 103 out of the catheter 102, and (C) the deployed device fills the vessel lumen 104. FIGS. 1(D-F) show in vitro demonstration of an embodiment of VOD deployment showing immediate expansion of the VOD foam 102' in 37° C. (body temperature) water in a silicone tube (3.5 mm inner diameter) after deployment from catheter 103'.

Figure 2:
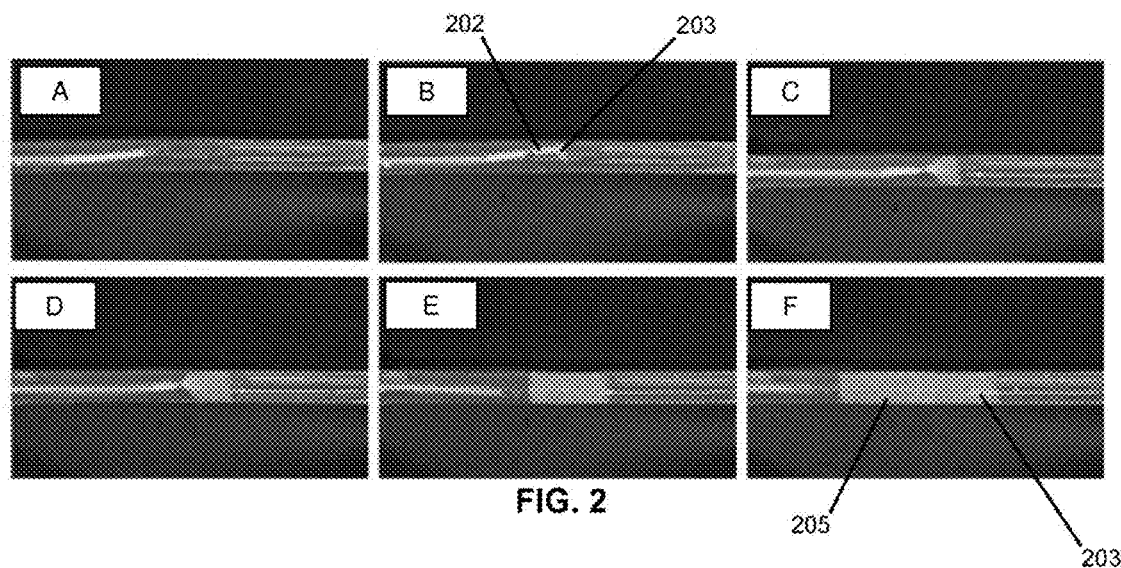
FIGS. 2(A)-(F) depict deployment of embodiments.

FIG. 2 shows a bulk foam device navigated through the catheter 202 (A), distal tip of the device exposed to circulating flow (B), distal tip of foam 203 completely expanded and apposed to vessel wall (C), unsheathing the device (D), the device completely deployed (E), and subsequent delivery of a second device 205 (F).

Figure 3:
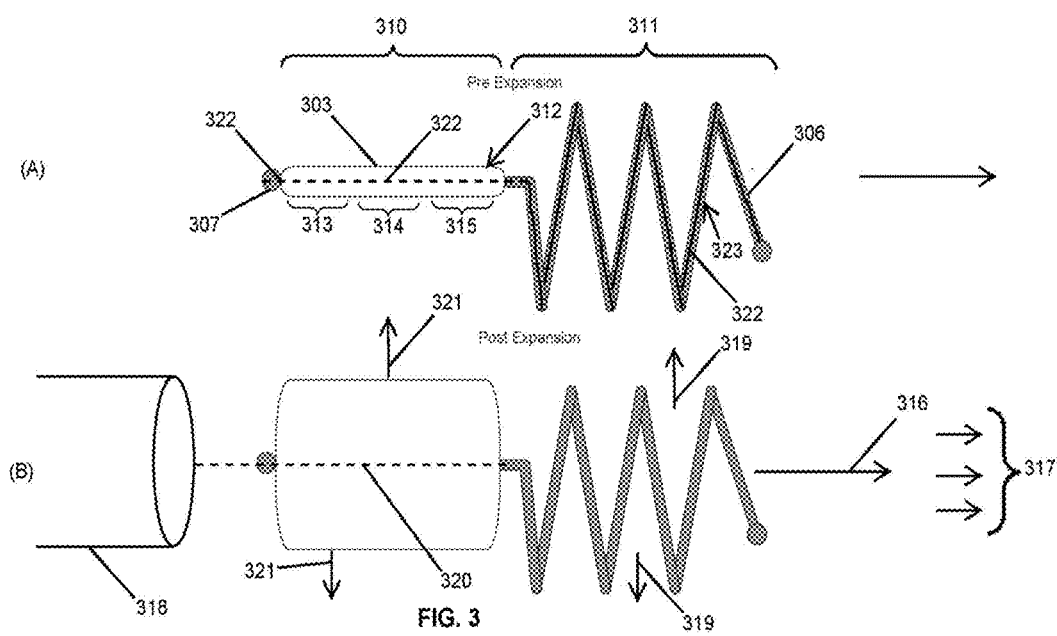
FIGS. 3(A)-(B) depict a shape memory polymer foam with an anchor in pre and post expansion conditions.

FIG. 3 shows a device embodiment that consists of a shape memory polymer foam 303 plug with a leading edge coil anchor 306 (distal) and a proximal radiopaque marker 307.

Figure 4:
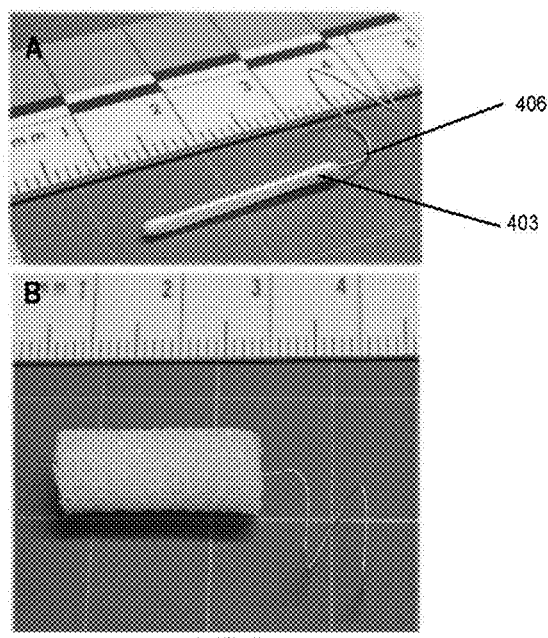
FIGS. 4(A)-(B) depict a shape memory polymer foam with an anchor in pre and post expansion conditions.

FIG. 4 shows a crimped (A) and expanded (B) device embodiment which consists of a shape memory polymer foam plug 403 with a distal coil anchor 406 that extends through the core of the device.

Figure 5:
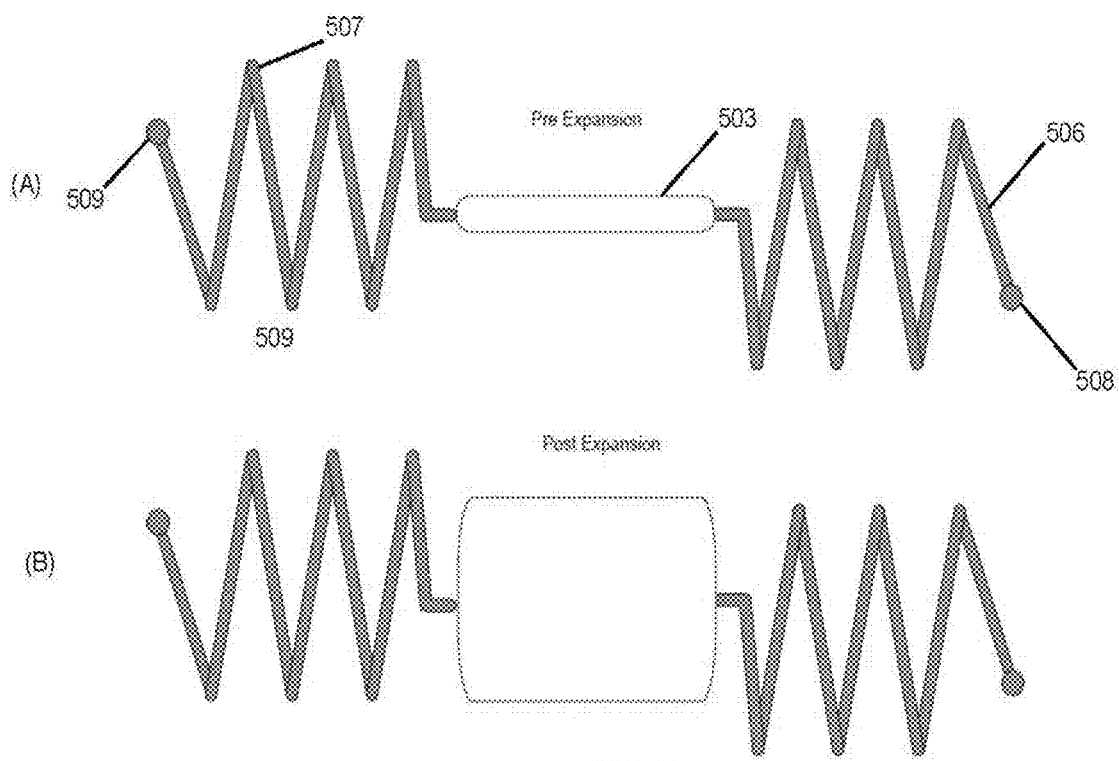
FIGS. 5(A)-(B) depict a shape memory polymer foam with dual anchors in pre and post expansion conditions.

FIG. 5 shows a device embodiment that consists of a shape memory polymer foam 503 plug with a proximal 506 and distal 507 coil anchor. In an embodiment the anchors include radiopaque markers 508 and/or 509.

Figure 6:
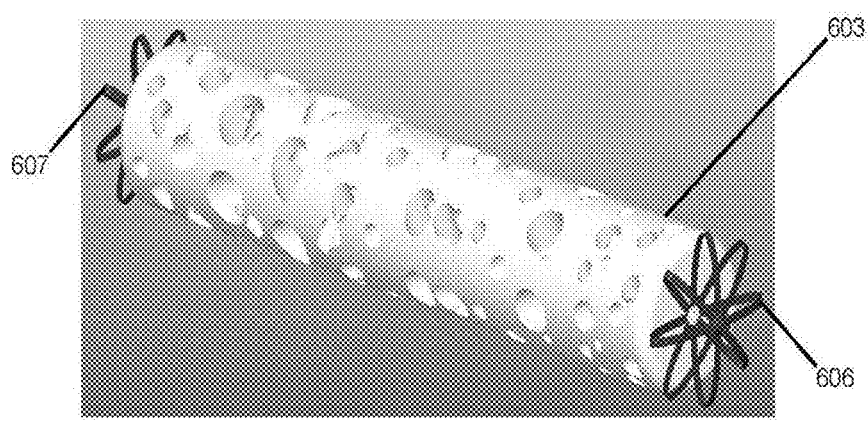
FIG. 6 depicts an embodiment including flower shaped anchors.

FIG. 6 shows a device embodiment that consists of a shape memory polymer foam plug 603 with proximal and distal flower-shaped anchors 606, 607 cut from a monolithic tube of nitinol.

Figure 7:
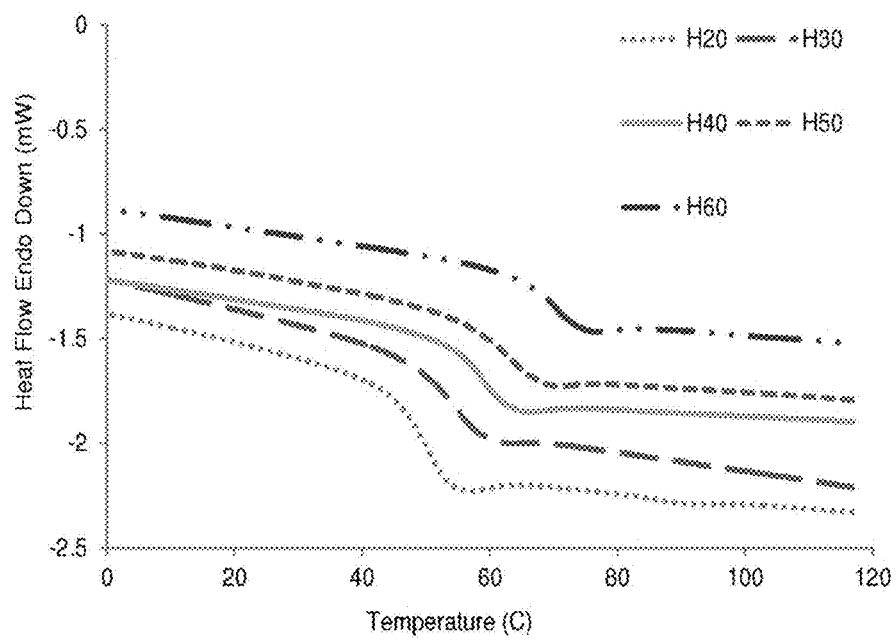
FIG. 7 shows thermomechanical analysis of various foam formulations.

FIG. 7 shows thermomechanical analysis of various foam formulations used in device fabrication, which demonstrate the tunability of the glass transition temperature of the device.

In greater detail, differential scanning calorimetry (DSC) was used to assess the ability to control the activation temperature of embodiments, which corresponds to the Tg of the materials of the embodiments. It is critical that the actuation temperature of these devices is greater than the temperature at which they are stored to prevent premature expansion of the foams. The Tg for all foam formulations ranged between 49 and 70° C. FIG. 7 shows representative thermograms for each foam composition used, where H20-H60 correspond to foam compositions with 20-60% molar equivalents of HPED. The thermograms demonstrate a single transition with no indication of a secondary transition, as well as a nearly linear relationship between increasing Tg as the ratio of HPED to TEA also increases. The average Tg ranged from H20 (49.85° C.) to H60 (69.44° C.).

| Foam Composition | Average Tg (° C.) | Standard Deviation |
| --- | --- | --- |
| H20 | 49.84 | 0.15 |
| H30 | 53.33 | 0.58 |
| H40 | 58.83 | 0.28 |
| H50 | 62.49 | 0.26 |
| H60 | 69.44 | 0.39 |

Devices fabricated using H20 and H30 formulations expanded too rapidly to allow delivery of devices via catheter. For this reason, some embodiments include H40, H50, and H60 foams. There is a general trend of decreasing expansion rate, within the first three minutes of submersion in 37° C. water, as the crosslink density of the foam increases (higher HPED content). The first three minutes of exposure to aqueous environments is critical in embodiments designed to be delivered within three minutes after first contacting blood or saline. Pore size also had a dramatic effect on expansion rate where expansion rate decreased as the pore size decreased due to increased foam density delaying water diffusion into the foam matrix. However, regardless of pore size and foam composition, all samples experienced 100% shape recovery in less than 20 minutes.

Figure 8:
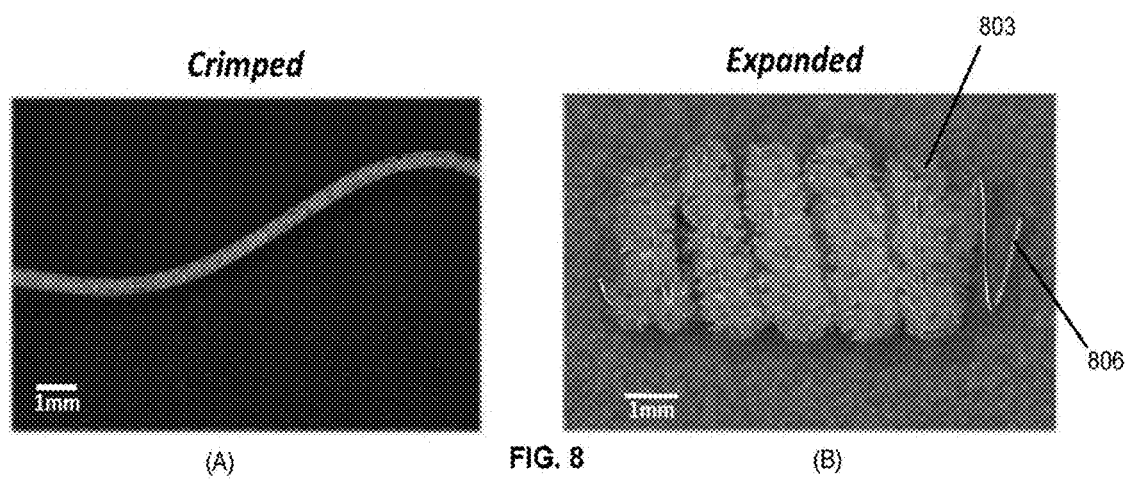
FIGS. 8(A)-(B) depict a shape memory polymer foam on a coil in pre and post expansion conditions.

FIG. 8 shows a crimped and expanded image of a foam-over-coil embodiment of the embolization device where a coil 806 is placed centrally through the core of a cylindrical piece of foam 803.

Figure 9:
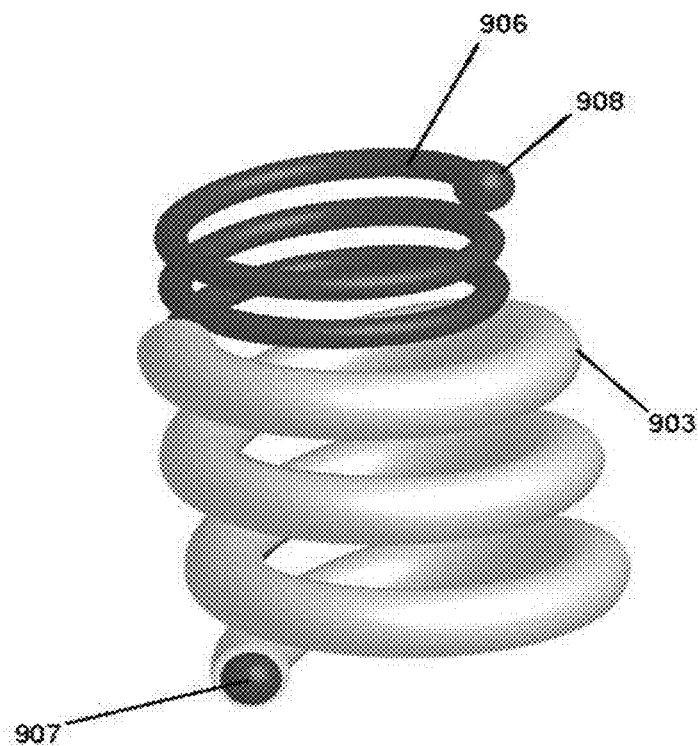
FIG. 9 depicts a shape memory polymer foam on a coil.

FIG. 9 shows an illustration of the foam-over-coil embodiment of the embolization device where a coil 906 is placed centrally through the core of a cylindrical piece of foam 903 and there is a distal section of exposed coil without foam. An embodiment includes radiopaque markers 908 and/or 907.

Figure 10:
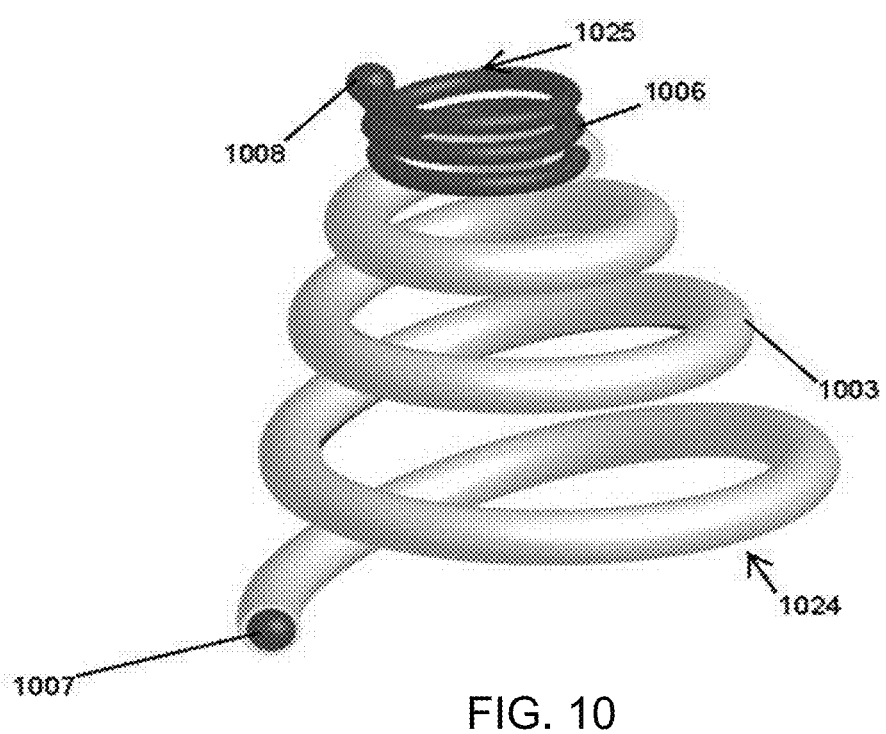
FIG. 10 depicts a shape memory polymer foam on a conical coil.

FIG. 10 shows an illustration of the foam-over-coil embodiment of the embolization device where a coil 1006 is placed centrally through the core of a cylindrical piece of foam 1003 and the diameter of coil gradual increases towards one end of the device similar to a spiral. An embodiment includes radiopaque markers 1008 and/or 1007.

As described herein, through the use of DSC, embodiments allow precise control of the actuation temperature of SMP foams by altering the ratio of HPED to TEA. The increase in Tg as the amount of HPED increases is a result of the increased crosslink density associated with additional HPED and the steric hindrance provided by the molecular structure of HPED which limits chain mobility. The ability to control the Tg of SMP foam devices is highly useful for controlling the actuation rate of the device when exposed to circulating blood. This provides a simple means of altering the expansion kinetics of the foam to satisfy the unique specifications required by clinicians for different device indications.

Since the activation of SMPs is entropy-driven and body temperature is lower than the Tg of each foam formulation, some embodiments of the polymers must experience plasticization in the blood or saline injection inside the delivery catheter in order to depress the Tg sufficiently to initiate expansion. Although the transition temperature of these foams are significantly greater than 37° C., the Tg of the foams is depressed to approximately 10° C. when exposed to 100% humidity. This transition temperature depression is what allows the foams to expand in the 37° C. aqueous environment within the body. The expansion studies demonstrated the ability to tune the working time of the proposed device, defined as the point at which the expanded diameter of the foam is four times the inner diameter of the delivery catheter. By altering the ratio of HPED to TEA during foam fabrication and the foam pore size, devices can be fabricated with working times varying from one to five minutes.

An average burst pressure of human saphenous veins is approximately 1,575 mm Hg. Based on this burst pressure and a PED 8 mm in diameter and 2 cm long device, the radial force of the foams must not exceed 107N to prevent vessel rupture in the venous system. This maximum radial force assumes a uniform distribution of radial force exerted along the length and circumference of the device. Based on this information, radial force tests demonstrated that the SMP foams exert a radial force on the vessel wall that is drastically smaller than would be required for vessel rupture. This is also considering that the foams are oversized by 50% to the inner diameter of the vessel, which is the common sizing practice when selecting an appropriately sized vascular plug. This test demonstrated that the risk of rupturing the target vessel with this device as a result of foam expansion is extremely low, regardless of which foam formulation is used. The more likely device component to cause vessel perforation or rupture is the coil anchor. Although the radial force of the coil exceeds that of foam, it exerts nearly an order of magnitude less force than commercially available vascular plugs used for peripheral occlusion, as well as less than 50% of the pressure required to rupture saphenous vein grafts and approximately 50% less pressure than FDA-approved embolic plugs currently on the market. The mechanical forces exerted by the PED implicate that the risk of vessel rupture as a result of the coil anchor is low.

Device migration studies demonstrated that embodiments are at least as stable as Cook Nester® Coils. Although embodiments provided equal or superior resistance to undesired thromboembolism, device stiffness testing demonstrated that the embodiments are significantly less stiff than current embolic plugs used on the market, such as the AVP II. The reduction in stiffness and use of a coil anchor for stability rather than an expandable nitinol mesh, allows the PED embodiments to be delivered to small, tortuous vessels that may not be accessible to other embolic plugs due to the risk of catheter deflection and excessive force required to advance the device.

Embodiments of the SMP foams provide sufficient echogenicity to enable delivery using ultrasound guidance. The ability to deliver these devices using ultrasound guidance also allows for embodiments consisting entirely of SMP foam with no metallic components that can still be delivered and visualized using endovascular techniques. Although dependent on the depth of the treatment vessel within the body, ultrasound imaging provides a means of delivering these devices without subjecting the patient to any radiation or potential side effects of the contrast injections required during fluoroscopy.

In vitro blood perfusion studies and the subsequent histological analysis of SMP foam devices revealed that blood penetrated throughout the device. No foam sections appeared to be devoid of thrombus deposition, and a dense fibrin mesh was clearly visible at proximal, middle, and distal locations of the device at the moment in which complete vessel occlusion occurred. Complete occlusion was witnessed after 270 seconds of blood perfusion through the device. The pressure setting used in this experiment (450 mmHg) served as a rigorous test of in vitro clotting of the device as flow would likely be diverted, thereby creating clinical occlusion, from the treatment vessel at much lower pressures in vivo. Considering the absence of tissue factor VII and any influence from the extrinsic clotting cascade on thrombus formation, complete occlusion in less than five minutes is a significant achievement; especially considering certain FDA-approved peripheral embolization devices may require more than 5 minutes to achieve vessel occlusion.

Embodiments discussed herein show the mechanical properties of the shape memory polymer PED device are safe and unlikely to cause vessel perforation or rupture. At the same time, these studies demonstrated that the likelihood of device migration and undesired thromboembolism to be minimal. Embodiments accomplished this while also demonstrating a significant reduction in overall device stiffness compared to commercially available vascular plugs, which allows embodiments to be delivered to tortuous vessels that may not be accessible using conventional embolic devices. Embodiments cause complete vessel occlusion and encourage rapid thrombus formation, and demonstrate ease of visualization of the PED using ultrasound and/or fluoroscopy and the like.

Figure 12:
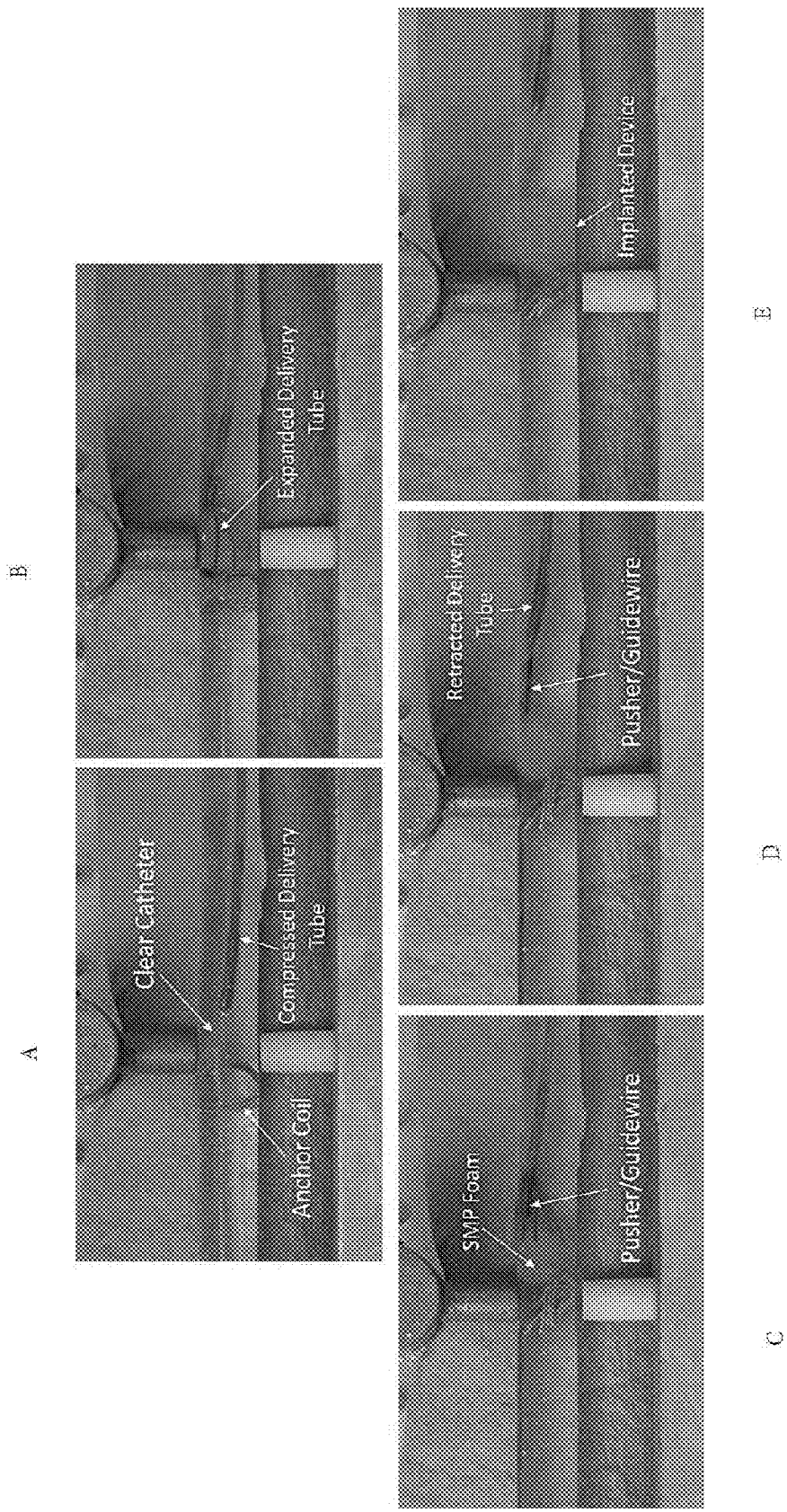
FIGS. 12(A)-(E) depict deployment of an embodiment.

FIG. 12(A) includes an embodiment similar to FIG. 3(A). For example, a coil (in its primary shape) has been deployed from a catheter. The SMP foam has not yet been ejected or deployed from the catheter. In FIG. 3(B) the SMP foam has been deployed from the catheter upstream of the coil. In this embodiment the foam is deployed within a cage structure ("expanded delivery tube"). This tube may have splines or struts that, upon no longer being constrained by the catheter, open radially to project force against the vessel walls (possibly helping spread apart walls that have partially collapsed). The splines may be superelastic. The splines may include, for example, stainless steel or nitinol. The foam expands to its primary shape while still within (partially or completely) the struts of the cage structure.

If the physician determines the foam is improperly deployed, the physician may withdraw the cage back into the catheter and in so doing, have the cage arms or splines collapse around the misplaced foam and withdraw the foam into the catheter. In such a case the guidewire (used to deploy the foam from the "expanded delivery tube" and ultimately deliver the device to the vessel) and the cage may be separate from one another. The guidewire and cage may be withdrawn simultaneously, or the cage may be withdrawn while the guidewire position is maintained prior to the guidewire withdrawing into the catheter.

As seen in FIG. 12(C), if the foam is properly placed the guidewire may remain deployed (thereby keeping the foam deployed) while the cage is withdrawn causing the cage to collapse within the catheter. This has begun to occur in FIG. 12(C) and is continuing in FIG. 12(D). As shown in FIG. 12(D), the foam remains coupled to the coil anchor (via a metal backbone) and, if the foam moves downstream, the foam will move towards the coil anchor. In FIG. 12(D) the guidewire is clearly shown further deployed (closer to anchor) than the cage.

As noted above, the guidewire may merely push against a proximal portion of a metal backbone (i.e., the guide wire is not fixedly coupled to the backbone) that couples to the anchor or the guidewire. However, in other embodiments the guide wire may have an electrolytic release from the backbone and the like (e.g., guidewire couples to the backbone at a node that can be terminated via electrolytic process/ reaction). The guidewire may couple via threads whereby the guidewire and backbone have complementary threads for coupling to each other.

FIG. 12(E) shows the catheter, cage, and guidewire being withdrawn away from the deployed anchor and foam (labeled "Implanted device").

In an embodiment the cage frame may be a monolithic design fabricated from a single, continuous material. For example, the struts may be formed from a single, continuous tube, where the struts are cut and positioned from the tube. In some embodiments, the cage may have 2-30 struts. The struts may have a free end (shown distal or downstream) and a fixed end where they couple to a portion of the tube that has not been cut. In other words, their distal ends may be free from each other while their proximal ends all terminate at a band that is a portion of a tube from which the arms were formed.

The struts may be constructed of elastic, biocompatible materials having a high strain recovery. In some embodiments, a shape memory alloy having a strain recovery of 3% may be used (however other embodiments are not so limited and may include shape memory elements with strain recovery of 4%, 6%, 8%, 10% or more). Materials that may be used include, but are not limited to: shape memory alloys; titanium alloys, such as nitinol; copper-base alloys, such as Cu—Al—Ni; platinum alloys, such as Fe—Pt; chromium-cobalt alloys, such as Co—Cr—Mo; cadmium-base alloys, such as Ag—Cd; shape memory polymers, such as urethane; and stainless steel. The struts may be comprised of combinations of materials; for example, the proximal segment may be nitinol, the intermediate segment may be stainless steel, and the distal segment may be Co—Cr—Mo.

To make the cage structure an embodiment entails cutting a plurality of slots into an elastic tube. Cutting slots in a tube, wire, or rod may create the form of struts. For devices having continuous struts down the device frame, a single set of slots may be cut. The struts may be cut by a laser or other precision cutting device. The device cage frame may be shape set. Shape setting may involve creating a permanent shape for the device cage frame. For metal frames, shape setting may include molding the device frame to an expanded shape to which the device returns when radial restrictions are removed, such as through deployment from a tube. The device frame shaping may include forming a device frame and heat treating the device frame. Device formation may be performed by setting the tube in a mold structure and compressing the tube so that the struts expand into a preconfigured shape. Spacers corresponding to desired structure length may be placed in the corresponding section of tube; for example, a 10 mm spacer may be placed in a section of tube corresponding a proximal structure, where the desired proximal structure length is 10 mm. An external frame tailored to the desired structure diameter may be placed around the corresponding section of tube. The tube may be compressed axially until the lateral struts contact the external frame and/or the internal radial struts contact the spacer. The process may be applied subsequently or concurrently to other sections of the device frame. After formation of the preconfigured shape, the device may be heat treated to create a permanent shape to which the device frame will return to once external restrictions are removed.

The following examples pertain to further embodiments.

Example 1 includes an embolic device, wherein the device is used to stably occlude the flow of blood within a vessel undergoing treatment.

Example 2 includes the embolic device of example 1, wherein the clot formation and stable occlusion occurs within 0-30 minutes after deployment of the device.

Example 3 includes the embolic device of example 1, wherein the device is delivered and deployed in the treatment region in a time frame of 5 seconds to 30 minutes.

Example 4 includes the embolic device of example 1, wherein the device is composed of a polyurethane SMP.

However, other embodiments may use a hydrogel or like in place of the SMP foam.

Example 5 includes the embolic device of example 4, wherein the polymer is fabricated using a combination of hexamethylene diisocyanate (HDI), trimethylhexamethylene diisocyanate (2,2,4- and 2,4,4-mixture) (TMHDI) N,N,N',N'-Tetrakis(2-hydroxypropyl)ethylenediamine (HPED), and 2,2',2''-nitrilotriethanol (TEA).

Example 6 includes the embolic device of example 1, wherein the occlusion occurs as a result of flow stagnation of the blood caused by the morphology of the device.

Example 7 includes the embolic device of example 1, wherein the occlusion occurs as a result of the tissue injury response of the endothelium of the vessel to device implantation and the exposure of tissue factor binding sites.

Example 8 includes the embolic device of example 1, wherein the occlusion occurs as a result of recirculation zones within the blood flow caused by the morphology of the implant.

Example 9 includes the embolic device of example 1, wherein the occlusion occurs as a result of platelet aggregation and activation throughout the volume of the device.

Example 10 includes the embolic device of example 1, wherein the device is made from a shape memory foam.

Example 11 includes the embolic device of example 1, further comprising an anchor that holds the device in place within the blood vessel.

Example 12 includes the embolic device of example 11, wherein the anchor is placed proximal, distal, or at both locations relative to the device.

Example 13 includes the embolic device of example 11, wherein the anchor comprises nitinol, platinum, stainless steel, polycarbonate, or a combination of these materials.

Example 14 includes a delivery mechanism, wherein the delivery mechanism delivers the embolic device of example 1 to an area needing treatment, and remains at the location until the embolic device has expanded to create an occlusion.

Example 15 includes the delivery mechanism of example 14, wherein the delivery mechanism is a catheter, expanding balloon catheter, or a guidewire.

Example 16 includes the delivery mechanism of example 14, wherein the device is crimped over the core wire to provide sufficient friction between the implant and core wire to allow retraction and advancement of the device until it is fully expanded in the lumen of the treatment vessel.

Example 17 includes the delivery mechanism of example 14, wherein the core wire is a stainless steel, nitinol, steel alloy, polypropylene, polytetrafluoroethylene, or nylon wire, or a combination of these materials comprising a braided wire or coil.

Example 18 includes the delivery mechanism of example 14, wherein the core wire is between 0.0005 and 0.050 inches in diameter.

Example 19 includes the device of example 5 wherein the foam includes radiopaque fillers, such as iodine, tungsten, platinum, barium sulphate, or any combination of these compounds.

Example 20 includes the device of example 5 wherein the morphology and surface chemistry of the device causes fibrin deposition and platelet aggregation in less than 180 seconds.

Example 21 includes the anchor of example 12 wherein the anchor geometry comprises a helix, spiral, or a helix with gradually increasing diameters over the length of the device.

Example 22 includes the anchor of example 12 wherein the anchor comprises a cylindrical tube that is cut such that it contains a plurality of struts that may extend outward from the original cylinder geometry.

Example 23 includes the device of example 4 wherein the device is modified such that interconnected pathways are created through the SMP.

Example 1a includes a system comprising: an outer conduit having proximal and distal ends; a shape memory polymer (SMP) foam having proximal and distal ends and that transitions from a secondary shape to a primary shape when the SMP foam is heated above its glass transition temperature (Tg); a metal backbone including: (a)(i) a first portion that extends from the SMP foam proximal end to the SMP foam distal end and which is generally covered by the SMP foam, and (a)(ii) a distal portion that extends distally from the SMP foam distal end and which is not covered by the SMP foam; wherein: (b)(i) SMP foam and the metal backbone are both included within the outer conduit adjacent to the outer conduit distal end; (b)(ii) the metal backbone distal portion transitions from a secondary shape that is uncoiled to a primary shape that is coiled; and (b)(iii) the metal backbone distal portion is in the metal backbone distal portion secondary shape and is located between the SMP foam distal end and the distal end of the outer conduit.

For instance, the outer conduit may include an introducer sheath or lumen that fits within a catheter or some other lumen. In an embodiment the system is delivered to the end user in a contained package that includes the SMP foam already "loaded" within the introducer sheath and near a distal end of the sheath so the SMP foam can be deployed from the sheath with minimal distance to traverse. In this case, the "distal" end is the end of the device furthest from the physician when the physician is deploying the device. The primary shape of the SMP foam may be an expanded cylinder such as the cylinder shown in the post-expansion diagram of FIG. 3. The primary shape of the metal backbone distal portion may be a coil as shown in FIG. 3. Further, the Tg may depress due to plasticization.

For instance, in FIG. 3 the metal backbone includes a portion (e.g., portion 310) that extends from the SMP foam proximal end to the SMP foam distal end and which is generally covered by the SMP foam 303. The metal backbone may also include a portion 311 that extends distally from the SMP foam distal end 312 and which is not covered by the SMP foam.

Figure 11:
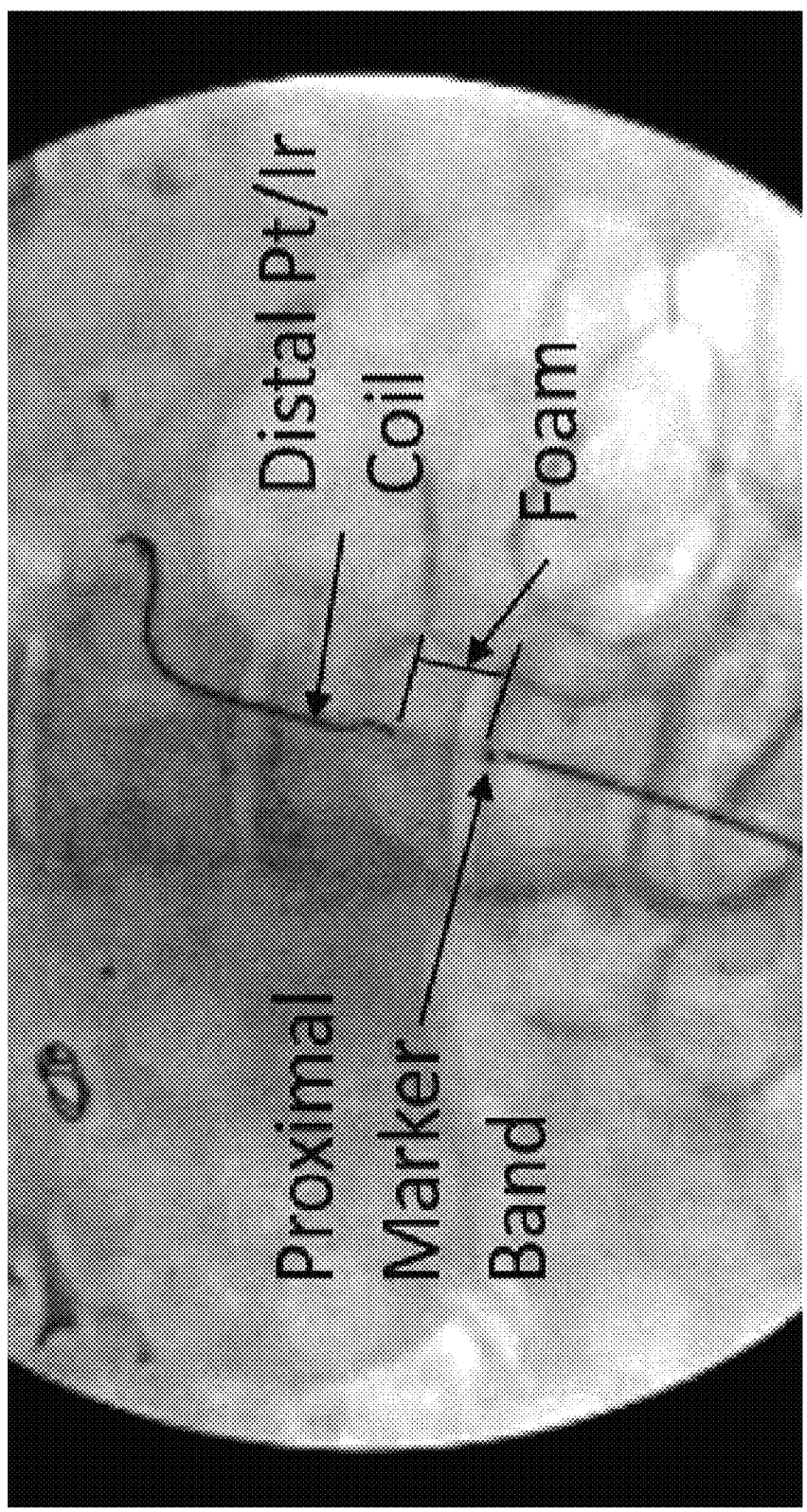
FIG. 11 depicts an image of an embodiment before the anchor of the embodiment has fully deployed.

For instance, the metal backbone distal portion transitions from a secondary shape that is uncoiled. FIG. 11 shows the secondary shape (see "Distal Pt/Ir Coil") when the distal anchor is still within a catheter (or at least a portion of the anchor is still in the catheter) and has not yet been unconstrained such that it may return to its primary shape of a coil.

As used herein Tg refers to the specific "glass transition temperature" whereas the "transition temperature" can refer to the Tg, the melt transition, or a crystallization temperature, among others. In an embodiment the SMP foam actuates at the Tg but may actuate at melt temperatures in other embodiments.

Another version of Example 1a includes a system comprising: an outer conduit having proximal and distal ends; a shape memory polymer (SMP) foam having proximal and distal ends and that transitions from a secondary shape to a primary shape when the SMP foam is heated above its transition temperature; a metal backbone including: (a)(i) a first portion that extends from the SMP foam proximal end to the SMP foam distal end and which is generally covered by the SMP foam, and (a)(ii) a distal portion that extends distally from the SMP foam distal end and which is not covered by the SMP foam; wherein: (b)(i) SMP foam and the metal backbone are both included within the outer conduit adjacent to the outer conduit distal end; (b)(ii) the metal backbone distal portion transitions from a secondary shape that is uncoiled to a primary shape that is coiled; and (b)(iii) the metal backbone distal portion is in the metal backbone distal portion secondary shape and is located between the SMP foam distal end and the distal end of the outer conduit.

In an embodiment the transition temperature equals the Tg for the SMP foam.

Example 2a includes the system of example 1, wherein the SMP foam is a polyurethane SMP foam that includes N,N,N',N'-tetrakis (2-hydroxypropyl) ethylenediamine (HPED), triethanolamine (TEA), and hexamethylene diisocyanate (HDI).

For instance, aside from the HDI the ratio of HPED to TEA may be used to tailor the expansion rate. Expansion rates may be short (e.g., 1, 3, 5, 7, 9 min) or longer (e.g., 20, 25, 30 min or longer). Embodiments may include, for example, a range of 20 molar percent HPED to TEA all the way up to 80 molar percent HPED to TEA. Thus, embodiments may have ratios of moles of HPED to TEA of 0.2-0.8. However, other embodiments go outside those bounds.

Other embodiments may include wherein the SMP foam includes N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

Other embodiments may include wherein the SMP foam includes N,N,N',N'-tetrakis (2-hydroxypropyl) ethylenediamine (HPED), Glycerol, pentanediol, and hexamethylene diisocyanate (HDI).

Example 3a includes the system of example 2 wherein the metal backbone distal portion includes an outer metal portion, including a channel, and an inner metal portion included within the channel.

For instance, see above for a description of how platinum/iridium coils were threaded over superelastic nitinol wire. For instance, see inner metal portion 322 within outer metal portion 323 of FIG. 3.

Example 4a includes the system of example 3, wherein: the metal backbone first portion also includes the inner metal portion but does not include the outer metal portion; and the inner metal portion is monolithic and extends from the SMP foam proximal end, to and through the SMP foam distal end, and into the channel of the outer metal portion distal to the SMP foam.

For instance, the inner metal portion may be a long monolithic (formed of one piece without seams or welds) wire that extends through the foam (area 310) and into the channel of the outer metal portion (area 311) while the outer metal portion may be restricted to area 311. As shown in FIG. 11, the outer metal portion may include platinum or iridium to provide radiopacity, which may be lacking for the inner metal portion (which may include, for example, nitinol) and foam.

This may be true for the embodiments of FIGS. 9 and/or 10 as well. For example, the portions not covered by foam may include the outer metal portion over the inner metal portion and the parts that are covered by foam may only include the inner metal portion.

Also, when delivering an embodiment under ultrasound, both the SMP and platinum coil anchor provide sufficient echogenicity to allow visualization. Significant acoustic shadowing indicative of an acoustically dense material was witnessed, providing further evidence that the embodiment is likely to cause rapid occlusion upon expansion in vivo. This shadowing is the same phenomenon used by physicians to identify dense, calcified lesions within arteries with intravascular ultrasound (IVUS).

Example 5a includes the system of example 4, wherein at least a portion of the outer metal portion is more radiopaque than both the inner metal portion and the SMP foam.

Example 6a includes the system of example 5, wherein the inner metal portion is superelastic.

For instance, the inner metal portion may include nitinol. Superelasticity may also be referred to pseudoelasticity. As used herein, it is a property unique to shape memory alloys where they can reversibly deform to strains as high as 10%. This deformation characteristic does not require a change in temperature (like the shape memory effect), but the material needs to be above the transformation temperature to have superelasticity.

Example 7a includes the system of example 6, wherein: the SMP foam includes a proximal portion that includes the proximal end of the SMP foam and a distal portion that includes the distal end of the SMP foam; and one of the proximal and distal portions of the SMP foam fixedly adheres to the metal backbone first portion and another of the proximal and distal portions of the SMP foam slideably couples to the metal backbone first portion.

For instance, in FIG. 3 the SMP foam may be epoxied or otherwise adhered to backbone portion 310 at areas 313 and/or 314 and/or 315. Adhering the foam at only one of the locations allows the foam to travel along the backbone while expanding radially. Thus, in an embodiment the foam slightly shrinks linearly when expanding radially. Further, adhering the foam at some location helps ensure the foam stays coupled to the anchor if, for example, a user opts to deploy the system such that the foam is located downstream of the anchor.

Example 8a includes the system of example 7, wherein the SMP foam and the metal backbone distal portion are oriented with respect to each other and with respect to the outer conduit so the metal backbone distal portion deploys from the distal end of the outer conduit before the SMP foam deploys from the distal end of the outer conduit.

For instance, in FIG. 3 the system is deployed from catheter 318 in the distal direction 316 into or towards downstream blood pressure (i.e., blood is moving in direction 317). In this case, the anchor 306 is able to form the "leading edge" and points "downstream" whereas foam 303 is located upstream of the anchor. This is beneficial in that any downstream movement of foam 303 will actually push the foam towards the anchor and in so doing will cause the coil to produce greater radial force 319, thereby driving the coil further into the vessel thereby stabilizing the system and preventing the system from moving downstream. This added force into the endothelial lining of the vessel may further illicit a healing response described herein.

To ensure embodiments had a limited risk of migrating downstream and causing unintended thrombosis, studies were conducted in which the maximum flow rate was determined for each embodiment size for comparison to a conventional embolic coil, Cook Medical's Nester® Embolic Coil. Results showed the embodiments can withstand equivalent or higher flow rates than Nester® coils. This analysis was also performed with only one Nester® coil within the mock vein, whereas at least three coils are typically implanted to achieve complete vessel occlusion in the clinic. If three coils were implanted into the test section, the pressure drop across the device mass would drastically increase, and the maximum flow rate for these coils would likely decrease further.

Example 9a includes the system of example 8 comprising a proximal metal portion that is: (c)(i) coupled to the inner metal portion, (c)(ii) located proximal to the SMP foam, (c)(iii) included within the outer conduit, and (c)(iv) is more radiopaque than both the inner metal portion and the SMP foam.

For instance, one such proximal metal portion may include node 307 of FIG. 3. Also see the "proximal marker band" of FIG. 11. In such a case, the physician can determine the location of the foam based on the "ghost" space between the band and the anchor (see "foam" of FIG. 11).

Example 10a includes the system of example 8, wherein at least one of the proximal metal portion and metal backbone includes an outer diameter that is at least 50% of an inner diameter of the outer conduit.

For example, the "Proximal marker band" of FIG. 11 may comprise a diameter 60, 70, 80, or 90% of the catheter or outer conduit within which it resides. Therefore a guide wire or pushing rod cannot easily slip between the marker band and the catheter wall. As a result, the guide wire or pushing rod easily couples to the device and can efficiently push the device out of the catheter.

Example 11a includes the system of example 8, wherein: the metal backbone first portion is aligned along an axis; and the metal backbone distal portion, in its primary shape, provides a radial force that is generally orthogonal to the axis and is greater than another radial force exerted by the SMP foam.

Such an axis is axis 320 of FIG. 3 and such a radial force of the anchor is force 319 and the radial force of the foam is force 321.

Radial force tests demonstrated that the radial force of foam devices consistently increased as the device diameter increases. The results for the radial force tests are summarized below.

| Foam Composition | Device Diameter (mm) | Vessel Diameter (mm) | Radial Force (N) |
|---|---|---|---|
| H40 | 4 | 2.7 | 0.08 ± 0.03 |
| | 6 | 4.0 | 0.16 ± 0.03 |
| | 8 | 5.3 | 0.24 ± 0.05 |
| | 10 | 6.7 | 0.30 ± 0.05 |
| H50 | 4 | 2.7 | 0.13 ± 0.07 |
| | 6 | 4.0 | 0.17 ± 0.04 |
| | 8 | 5.3 | 0.21 ± 0.04 |
| | 10 | 6.7 | 0.25 ± 0.03 |
| H60 | 4 | 2.7 | 0.20 ± 0.04 |
| | 6 | 4.0 | 0.29 ± 0.07 |
| | 8 | 5.3 | 0.38 ± 0.05 |
| | 10 | 6.7 | 0.36 ± 0.09 |

These tests show the radial force of SMP foams with varied foam chemistries (H40, H50, H60). A pore size of 0.5±0.1 mm was chosen for analysis of all chemistries after testing the radial force of foam samples with 0.5, 1, and 1.5 mm pore sizes, which revealed that foams with the smallest pore size exert the greatest radial force due to increased foam density. Constrained recovery tests demonstrated that the maximum force exerted on the vessel walls by foam expansion when the foam is 50% oversized to the target vessel is significantly lower than the 107N of force required to rupture autologous veins commonly used in bypass procedures, if we assume a uniform cylindrical surface area of the foam.

The radial stiffness of each different sized anchor was compared to the stiffness of two conventional vascular plugs. During radial force testing to determine device stiffness values, the 8 mm devices exerted an average maximum radial force of 4.0N, while the AMPLATZER™ Vascular Plugs (AVP II, St. Jude Medical, St. Paul, Minn.) exerted an average maximum radial force of 15.8N when oversized by 50% to the target vessel. Microscopic imaging of the 8 mm PED anchor coil revealed that approximately 30% of the coil surface area is in contact with the vessel endothelium, which corresponds to 0.43 cm2 of surface area. Given the estimated surface area of coils in contact with the vessel lumen, the PED anchor would exert a pressure of approximately 700 mmHg on the vessel endothelium-less than half the pressure required to cause rupture in an autologous vein graft. When a 16 mm AVP II was deployed within a flexible PVC tube with an inner diameter of 10 mm, it was estimated that approximately 0.85 cm2 of device surface area was in contact with the inner diameter of the tubing, resulting in a radial pressure of approximately 1,400 mmHg Given the proven safety and efficacy of the AVP II device that led to its FDA approval, and the markedly reduced radial force and pressure exerted by the PED anchor, it is unlikely that the PED coil anchor would cause vessel rupture or perforation in vivo. Prior to verification tests, it was hypothesized that the coil anchor would account for the vast majority of the radial force exerted by the PED. Radial stiffness testing revealed that this was indeed the case, as demonstrated by a maximum radial force of less than 0.5N for any foams tested.

Example 12a includes the system of example 8, wherein the outer conduit includes an introducer sheath.

Example 13a includes the system of example 8, wherein: the metal backbone first portion is aligned along an axis; and the SMP foam and the metal backbone distal portion are oriented with respect to each other so when upstream blood pressure forces the SMP foam towards the metal backbone distal portion the metal backbone distal portion, in its primary shape, presses radially outwards in a direction generally orthogonal to the axis and in response to the upstream blood pressure forcing the SMP foam towards the metal backbone distal portion.

Example 14a includes the system of example 8 with the TEA contributing a lower molar ratio of hydroxyl groups to the polyurethane SMP foam than the HPED.

Example 15a includes the system of example 8 with the TEA contributing a higher molar ratio of hydroxyl groups to the polyurethane SMP foam than the HPED.

Example 16a includes the system of example 15, wherein the polyurethane SMP foam includes a diisocyanate component consisting of the HDI and no other diisocyanate component.

For example, no TMHDI is used. This can be critical to promote rapid expansion of the foam in scenarios concerning traumatic injury where blood flow must be stopped quickly (e.g., less than 5 min or even less than 3 min).

Example 17a includes the system of example 8, wherein the outer metal portion includes at least one of platinum, palladium, tungsten, and iridium.

Example 18a includes the system of example 8 comprising an additional outer metal portion proximal to the SMP foam and not covered by the foam, wherein: the additional outer metal portion includes an additional channel; the inner metal portion extends to and through the SMP foam proximal end and into the additional channel; and the inner metal portion that extends to and through the SMP foam proximal end and into the additional channel also transitions from a secondary shape that is uncoiled to a primary shape that is coiled.

For example, see FIG. 5. In such a case, the inner metal portion may be a single nitinol wire that extends throughout the length of the foam and into platinum coatings (e.g., outer metal portions) on both ends of the inner metal portion wire. In such a case, no marker bands may be needed as the physician can determine the location of the foam based on the "ghost" space between the two anchors.

Example 19a includes the system of example 8, wherein the metal backbone distal portion primary shape that is coiled includes a conically shaped coil with a base of the conically shaped coil between the SMP foam and a vertex of the conically shaped coil.

For instance, in FIG. 10 base 1024 may be ejected from the catheter or outer conduit after vertex 1025. In such an instance the base may be located upstream of the vertex. Further, a "conically shaped coil" as used herein includes a frustoconical shape (the basal part of a solid cone or pyramid formed by cutting off the top by a plane generally parallel to the base). Further, the coil of FIG. 3 may be conical with the base closer to the foam than the vertex or where the vertex is closer to the foam than the base. The same is true for either or both of the coils of FIG. 5 wherein either or both of the coils of FIG. 5 may be conical with the base closer to the foam than the vertex or where the vertex is closer to the foam than the base Example 20a includes a method comprising: providing a system comprising: an outer conduit having proximal and distal ends; a shape memory polymer (SMP) foam having proximal and distal ends and that transitions from a secondary shape to a primary shape when the SMP foam is heated above its glass transition temperature (Tg); a metal backbone including: (a)(i) a first portion that extends from the SMP foam proximal end to the SMP foam distal end and which is generally covered by the SMP foam, and (a)(ii) a distal portion that extends distally from the SMP foam distal end and which is not covered by the SMP foam; wherein: (b)(i) SMP foam and the metal backbone are both included within the outer conduit adjacent to the outer conduit distal end; (b)(ii) the metal backbone distal portion transitions from a secondary shape that is uncoiled to a primary shape that is coiled; and (b)(iii) the metal backbone distal portion is in the metal backbone distal portion secondary shape and is located between the SMP foam distal end and the distal end of the outer conduit; advancing the system into a patient; deploying the metal backbone distal end from the outer conduit distal end into a vessel of the patient; transitioning the metal backbone distal end from its secondary shape to its primary shape; engaging the metal backbone distal end with a wall of the vessel in response to transitioning the metal backbone distal end from its secondary shape to its primary shape; deploying the SMP foam from the outer conduit distal end into the vessel in response to deploying the metal backbone distal end from the outer conduit distal end; transitioning the SMP foam from its secondary shape to its primary shape; engaging the SMP foam with the wall of the vessel in response to transitioning the SMP foam from its secondary shape to its primary shape; and occluding the vessel in response to engaging the SMP foam with the wall of the vessel.

Another version of Example 20a includes a method comprising: providing a system comprising: an outer conduit having proximal and distal ends; a shape memory polymer (SMP) foam having proximal and distal ends and that transitions from a secondary shape to a primary shape when the SMP foam is heated above its transition temperature; a metal backbone including: (a)(i) a first portion that extends from the SMP foam proximal end to the SMP foam distal end and which is generally covered by the SMP foam, and (a)(ii) a distal portion that extends distally from the SMP foam distal end and which is not covered by the SMP foam; wherein: (b)(i) SMP foam and the metal backbone are both included within the outer conduit adjacent to the outer conduit distal end; (b)(ii) the metal backbone distal portion transitions from a secondary shape that is uncoiled to a primary shape that is coiled; and (b)(iii) the metal backbone distal portion is in the metal backbone distal portion secondary shape and is located between the SMP foam distal end and the distal end of the outer conduit; advancing the system into a patient; deploying the metal backbone distal end from the outer conduit distal end into a vessel of the patient; transitioning the metal backbone distal end from its secondary shape to its primary shape; engaging the metal backbone distal end with a wall of the vessel in response to transitioning the metal backbone distal end from its secondary shape to its primary shape; deploying the SMP foam from the outer conduit distal end into the vessel in response to deploying the metal backbone distal end from the outer conduit distal end; transitioning the SMP foam from its secondary shape to its primary shape; engaging the SMP foam with the wall of the vessel in response to transitioning the SMP foam from its secondary shape to its primary shape; and occluding the vessel in response to engaging the SMP foam with the wall of the vessel.

Example 21a includes the method of example 20, wherein: the metal backbone distal portion includes an outer metal portion, including a channel, and an inner metal portion included within the channel; at least a portion of the outer metal portion is more radiopaque than both the inner metal portion and the SMP foam; the method further comprising determining a position of the SMP foam within the vessel in response to at least a portion of the outer metal portion being more radiopaque than both the inner metal portion and the SMP foam.

Example 22a includes the system of example 8 including a plurality of resilient arm members that are free from one another at distal ends of the arm members and are fixedly coupled to each other at proximal ends of the arm members; wherein: the metal backbone first portion is generally aligned along an axis; at least a portion of the SMP foam is located within the plurality of arms such that a plane orthogonal to the axis intersects the SMP foam and the plurality of arms; the plurality of arms compresses within the outer conduit and expands radially when the arms deploy from the outer conduit.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

The invention claimed is:

1. A system comprising:
   an outer conduit having proximal and distal ends;
   a shape memory polymer (SMP) foam having proximal and distal ends and that transitions from a secondary shape to a primary shape when the SMP foam is heated above its transition temperature;
   a metal backbone including: (a)(i) a first portion that extends from the SMP foam proximal end to the SMP foam distal end and which is generally covered by the SMP foam, and (a)(ii) a second portion that extends distally from the SMP foam distal end and which is not covered by the SMP foam;
   wherein: (b)(i) the SMP foam and the metal backbone are both included within the outer conduit adjacent to the outer conduit distal end; (b)(ii) the metal backbone second portion is configured to transition from a secondary shape that is uncoiled to a primary shape that is coiled; and (b)(iii) the metal backbone second portion is in the metal backbone second portion secondary shape and is located between the SMP foam distal end and the distal end of the outer conduit;
   wherein (a) the metal backbone second portion includes an outer metal portion, including a channel, and an inner metal portion included within the channel, and (b) the metal backbone first portion also includes the inner metal portion but does not include the outer metal portion.

2. The system of claim 1, wherein the SMP foam is a polyurethane SMP foam that is a reaction product of N,N, N',N'-tetrakis (2-hydroxypropyl) ethylenediamine (HPED), triethanolamine (TEA), and hexamethylene diisocyanate (HDI).

3. The system of claim 2 with the TEA contributing a lower molar ratio of hydroxyl groups to the polyurethane SMP foam than the HPED.

4. The system of claim 2 with the TEA contributing a higher molar ratio of hydroxyl groups to the polyurethane SMP foam than the HPED.

5. The system of claim 4, wherein the polyurethane SMP foam includes a reaction product of a diisocyanate component consisting of the HDI and no other diisocyanate component.

6. The system of claim 1, wherein:
   the inner metal portion is monolithic and extends from the SMP foam proximal end, to and through the SMP foam distal end, and into the channel of the outer metal portion that is distal to the SMP foam.

7. The system of claim 6, wherein at least a portion of the outer metal portion is more radiopaque than both the inner metal portion and the SMP foam.

8. The system of claim 7, wherein the inner metal portion is superelastic.

9. The system of claim 8, wherein:
   the SMP foam includes a proximal portion that includes the proximal end of the SMP foam and a distal portion that includes the distal end of the SMP foam; and
   one of the proximal or distal portions of the SMP foam fixedly adheres to the metal backbone first portion and another of the proximal or distal portions of the SMP foam slideably couples to the metal backbone first portion.

10. The system of claim 9, wherein the SMP foam and the metal backbone second portion are oriented with respect to each other and with respect to the outer conduit so the metal backbone second portion deploys from the distal end of the outer conduit before the SMP foam deploys from the distal end of the outer conduit.

11. The system of claim 10 comprising a proximal metal portion that is: (c)(i) coupled to the inner metal portion, (c)(ii) located proximal to the SMP foam, (c)(iii) included within the outer conduit, and (c)(iv) is more radiopaque than both the inner metal portion and the SMP foam.

12. The system of claim 10, wherein at least one of the proximal metal portion or the metal backbone includes an outer diameter that is at least 50% of an inner diameter of the outer conduit.

13. The system of claim 10, wherein:
   the metal backbone first portion is aligned along an axis; and
   the metal backbone second portion, in its primary shape, provides a radial force that is generally orthogonal to the axis and is greater than another radial force exerted by the SMP foam.

14. The system of claim 10, wherein the outer conduit includes an introducer sheath.

15. The system of claim 10, wherein:
   the metal backbone first portion is aligned along an axis; and
   the SMP foam and the metal backbone second portion are oriented with respect to each other so when upstream blood pressure forces the SMP foam towards the metal backbone second portion the metal backbone second portion, in its primary shape, presses radially outwards in a direction generally orthogonal to the axis and in response to the upstream blood pressure forcing the SMP foam towards the metal backbone second portion.

16. The system of claim 10, wherein the outer metal portion includes at least one of platinum, palladium, tungsten, iridium, or combinations thereof.

17. The system of claim 10 comprising an additional outer metal portion proximal to the SMP foam and not covered by the foam, wherein:
   the additional outer metal portion includes an additional channel;
   the inner metal portion extends to and through the SMP foam proximal end and into the additional channel; and
   the inner metal portion that extends to and through the SMP foam proximal end and into the additional channel also transitions from a secondary shape that is uncoiled to a primary shape that is coiled.

18. The system of claim 10, wherein the metal backbone second portion primary shape that is coiled includes a conically shaped coil with a base of the conically shaped coil between the SMP foam and a vertex of the conically shaped coil.

19. The system of claim 10 including resilient arm members that are free from one another at distal ends of the resilient arm members and are fixedly coupled to each other at proximal ends of the resilient arm members;
   wherein:
      the metal backbone first portion is generally aligned along an axis;
      at least a portion of the SMP foam is located within the resilient arm members such that a plane orthogonal to the axis intersects the SMP foam and the resilient arm members;
      the resilient arm members compress within the outer conduit and expand radially when the resilient arm members deploy from the outer conduit.

* * * * *